June 27, 1972 W. H. JESSEL, JR., ET AL Plant Pat. 3,220
CHRYSANTHEMUM PLANT
Filed Oct. 12, 1970
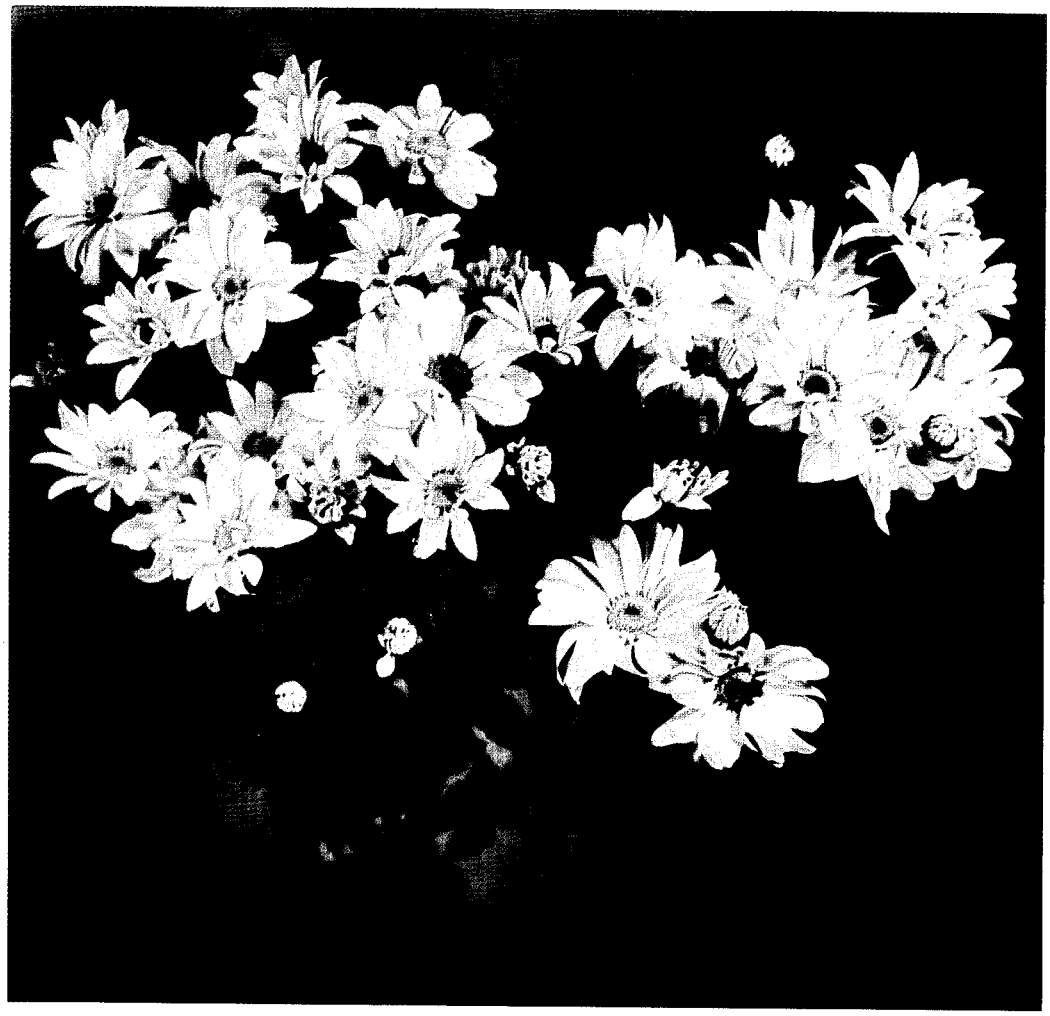
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,220
Patented June 27, 1972

3,220
CHRYSANTHEMUM PLANT

Walter H. Jessel, Jr., Doylestown, and William E. Duffett, Akron, Ohio, assignors to Yoder Brothers, Inc., Barberton, Ohio

Filed Oct. 12, 1970, Ser. No. 80,257
Int. Cl. A01h *5/00*
U.S. Cl. Plt.—74 1 Claim

The present invention comprises a new and distinct cultivar of chrysanthemum plant which is a sport of the unpatented cultivar known commercially in the United States as Bronze Marble.

The new cultivar is similar in many respects to Yellow Marble, an unpatented but commercial variety of Yoder Brothers, Inc., Barberton, Ohio, assignee herein, having the same characteristics as Yellow Marble of:

(1) Nine week response.
(2) Daisy flower form.
(3) Foliage color and shape.
(4) Tendency to set a low crown bud.

The new cultivar is distinguished from Yellow Marble by the following characteristics:

(1) Five inches to six inches shorter habit.
(2) Smaller foliage which is approximately 1½" shorter in length and 1" narrower in width.
(3) One-half inch smaller flowers.
(4) Twelve more flowers per spray.
(5) Darker yellow flower color which is more resistant to fading under high light, high temperature conditions.
(6) Flowers 2–3 days earlier in response with a more uniform response within a flowering block.
(7) During late summer, under high temperatures, its trait of heavy budding can result in a slower response of 3 days as compared to Yellow Marble.

The new cultivar was selected from a flowering block of the parent cultivar in Barberton, Ohio, and was asexually reproduced by cuttings in Barberton, Ohio. The new cultivar has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, total vigor, and color may vary significantly with varying environmental conditions such as temperature, day length, and light intensity. Suggested flowering in the northern and western United States is from May through October; California, April through mid-November; Florida and the deep south, December through April.

The accompanying photographic drawing shows the unique characteristics of my new cultivar, the color being as nearly true as possible with color illustrations of this type. The new cultivar appears on the left of the drawing and the comparison cultivar Yellow Marble on the right.

Color references herein are made to the Munsell Color Book, 1963 edition, and comparisons have been made where meaningful with Yellow Marble.

BOTANICAL CLASSIFICATION

*Chrysanthemum morifolium*

| | Gold Marble | Yellow Marble |
|---|---|---|
| Bloom: | | |
| Size | 2" | 2½". |
| Fully expanded | 2¾" | 3". |
| Borne | In compound lateral clusters of 8–12 flowers per lateral. | In compound lateral clusters of 5–8 flowers. |
| Stems | Wiry | Wiry. |
| Form | Daisy | Daisy. |
| Permanence | 7 days | 7 days. |
| Color (Munsell): | | |
| Center of flower | Light green, 2.5GY5/8 to dark yellow, 6.25Y8.5/12. | Light green, 2.5GY5/8 to dark yellow, 6.25Y8.5/12. |
| Base of petals | Dark yellow, 6.25Y8. 5/12. | Light yellow, 7.5Y9/6 to pale yellow, 7.5Y9/4. |
| Inside of petals | do | Do. |
| Reverse of petals | Yellow, 7.5Y8.5/10 | Pale yellow, 7.5Y9/4. |
| Tonality from a distance. | Golden yellow | Light yellow. |
| Discoloration | None | Pale yellow. |

Petals:

*Texture.*—Smooth.
*Appearance and form.*—Open at base—broad at midpoint tapering to a rounded point.
*Arrangement.*—Composite, whorled on a single receptacle.
*Persistence.*—Resist shatter.
*Fragrance.*—Typical chrysanthemum.

Reproductive organs:

*Stamen, anthers.*—200–250.
*Pollen.*—None to abundant (functional sterility).
*Arrangement.*—Clustered in center of flower, if present.
*Styles.*—Present in both ray and disc florets.
*Length.*—Short.
*Ovaries.*—At base of petal attached to receptacle.

| | Gold Marble | Yellow Marble |
|---|---|---|
| Plant: | | |
| Form | Herbaceous | Herbaceous. |
| Growth | Upright | Upright. |
| Height | Approximately 36-39" with 3-5 long day weeks and 12-14 week crop time for the various seasons as defined in the timetable of Yoder Brothers, Inc. | Approximately 42-47" with 3-5 long day weeks and 12-14 week crop time for the various seasons as defined in the timetables of Yoder Brothers, Inc. |
| Spread | None when grown single stem to moderate when pinched. | None when grown single stem to moderate when pinched. |

Foliage:

*Top side.*—Dark green, 7.5GY3/4.
*Size.*—5¾" long, 3¼" wide (Yellow Marble, by way of contrast, is 7¼" long, 4¼" wide).
*Quantity.*—Numerous.
*Shape.*—Spatulate lobed.
*Texture.*—Smooth.
*Ribs and veins.*—Prominent.
*Edge.*—Moderately indented.
*Serration.*—Moderate.
*Underside.*—Light green, 7.5GY5/4.
*Stipules.*—Prominent.

We claim:

1. A new and distinct cultivar of chrysanthemum characterized particularly in its points of uniqueness compared to the cultivar Yellow Marble by a 5"–6" shorter habit, smaller foliage which is approximately 1½" shorter in length and 1" narrower in width, higher production with approximately 12 more flowers per spray, a deeper yellow flower color which is more resistant to fade under high light and high temperature conditions, ½" smaller flowers, 2–3 days earlier response with a more uniform response within a flowering block, and a trait of heavy budding, which, under high temperature, late summer conditions, can result in a slower response of 3 days as compared to Yellow Marble.

No references cited.

ROBERT E. BAGWILL, Primary Examiner